(12) United States Patent
Leech et al.

(10) Patent No.: US 8,329,206 B2
(45) Date of Patent: Dec. 11, 2012

(54) BOLUS DEVICES FOR THE DELIVERY OF ACTIVE AGENTS TO ANIMALS

(75) Inventors: Wayne Frederick Leech, Auckland (NZ); William Ernest Pomroy, Palmerston North (NZ)

(73) Assignee: Bomac Research Limited, Manukau, Auckland (NZ)

( * ) Notice: Subject to any disclaimer, the term of this patent is extended or adjusted under 35 U.S.C. 154(b) by 0 days.

(21) Appl. No.: 13/131,259

(22) PCT Filed: Jun. 29, 2009

(86) PCT No.: PCT/NZ2009/000129
§ 371 (c)(1),
(2), (4) Date: Aug. 8, 2011

(87) PCT Pub. No.: WO2010/062190
PCT Pub. Date: Jun. 3, 2010

(65) Prior Publication Data
US 2011/0280923 A1    Nov. 17, 2011

(30) Foreign Application Priority Data
Nov. 25, 2008  (NZ) .................................... 573143

(51) Int. Cl.
*A61K 9/22* (2006.01)

(52) U.S. Cl. ........................................ 424/438; 424/468

(58) Field of Classification Search .................. None
See application file for complete search history.

(56) References Cited

U.S. PATENT DOCUMENTS 4,381,780 A      5/1983   Holloway
5,074,857 A  *  12/1991   Shepherd et al. .......... 604/891.1

FOREIGN PATENT DOCUMENTS

NZ        519363         2/2004
WO     WO 03/103636    12/2003

OTHER PUBLICATIONS

US 4,927,419, 05/1990, Scully et al. (withdrawn)

* cited by examiner

*Primary Examiner* — Suzanne Ziska
(74) *Attorney, Agent, or Firm* — Davis Wright Tremaine LLP; Dale C. Hunt; Sheila R. Gibson

(57) ABSTRACT

A bolus for administration of a substance to an animal, the bolus including An external coating, and A core inside the external coating wherein the core is formed from a plurality of dosage media, wherein each dosage media contains a substance, the bolus characterised in that the dosage media are ordered within the bolus such that the amount of substance released by each dosage media is progressively more than the amount of substance released by the previous dosage media.

9 Claims, 2 Drawing Sheets

BOLUS DEVICES FOR THE DELIVERY OF ACTIVE AGENTS TO ANIMALS

CROSS-REFERENCE TO RELATED APPLICATIONS

The present application is a U.S. National Stage entry under 35 U.S.C. §371 of International Application No. PCT/NZ2009/000129, filed on Jun. 29, 2009, designating the United States of America and published in English on Jun. 3, 2010, which in turn claims priority to New Zealand Patent Application No. 573143 filed on Nov. 25, 2008, each of which is hereby incorporated by reference in its entirety.

TECHNICAL FIELD

This invention has application to delivery devices for delivering medicaments to animals.

In particular, the present invention has application to boluses used to treat health conditions in animals.

BACKGROUND ART

It is well known in the veterinary field to use boluses to deliver medicaments to ruminants. Boluses can be used to treat specific ailments or as a preventative for specific conditions.

A bolus is a delivery device for the long term delivery of medicaments to an animal. Typically, the bolus consists of a housing with one open end, often made of plastic or metal alloy which contains a series of tablets. An example of such a bolus is disclosed in New Zealand Patent No. 220024 to Castex Products Limited.

The bolus is delivered into the stomach of the animal to be treated where the rumen fluids of the stomach act to erode the exposed tablet, thus releasing the medicament into the circulatory system of the animal.

Once all of the tablets have eroded, the housing (if made from metal) decays into its metal components and is usually passed through the animal by excretion. Some bolus housings made of plastic may be regurgitated whilst the animal is ruminating, or is retained by the animal in the rumen. The housing is made from biocompatible materials and thus is not harmful to the animal.

The tablets are designed to erode at relatively specific rates. This is to ensure that the animal does not receive particular medicaments in excess of a specific threshold, which may be harmful to the animal being treated. Exceeding a specific threshold of medicaments may also result in negative side effects for the animal being treated.

Boluses are ideal for the slow release of medicaments over time, thus avoiding the requirement to repeatedly dose the animal. Indeed, the bolus disclosed in New Zealand Patent No. 220024 is intended to remain in the rumen for several months.

As previously discussed, the release rate is designed to ensure that the medicament to be delivered does not exceed a certain threshold. This threshold is usually measured by the amount of medicament in the circulatory system of the animal relative to its body mass.

It will be appreciated therefore that a bolus intended for use with an adult cow may not be suitable for use with a calf, due to the difference in the body mass of these respective animals. The amount of medicament released by the bolus may in excess of what is considered to be a safe threshold for a calf.

Nor is a bolus intended for use with a calf suitable for the use with an adult cow, as the medicament delivered would be insufficient for the condition being treated in the adult cow.

In these instances, often the level of medicament which is intended to kill parasites or bacteria is not at a sufficient level to ensure complete eradiation of all the targeted parasites or bacteria. The remaining parasites or bacteria can build up resistance to the medicament, and thus over time the medicament may become unsuitable for treating the specific condition.

When raising cattle, it is economically beneficial to use methods which encourage rapid growth rates of juvenile cattle. Thus it is not uncommon for a calf to increase its body mass by more than 10% within a month. Because of the significant growth rates, it can be difficult to satisfactorily treat specific condition such as parasitic infestations.

It is an object of the present invention to address the foregoing problems or at least to provide the public with a useful choice.

Further aspects and advantages of the present invention will become apparent from the ensuing description which is given by way of example only.

All references, including any patents or patent applications cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements.

This rationale will also be used when the term 'comprised' or 'comprising' is used in relation to one or more steps in a method or process.

DISCLOSURE OF INVENTION

According to one aspect of the present invention there is provided a delivery device for administration of a substance to an animal, the delivery device including an external coating, and a core inside the external coating wherein the core is formed from a plurality of dosage media, wherein each dosage media contains a substance, the delivery device characterised in that the dosage media are ordered within the delivery device such that the amount of substance released by each dosage media is progressively more than the amount of substance released by the previous dosage media.

According to another aspect of the present invention there is provided a method of treating an animal, including the steps of, a) placing a delivery device containing a substance in the form of a plurality of dosage media in an animal's stomach, and b) releasing the dosage media sequentially in the animal's stomach, and wherein the dosage media chosen for delivery are ordered within the delivery device such that the ratio of substance released by the delivery device at a particular time to the estimated body mass of the animal at that time remains substantially constant.

The invention broadly relates to a delivery device primarily for use in non-human animals which deliver a substance to the animal. Preferably, the non-human animal is a ruminant.

Preferably, the delivery device is a bolus, and reference shall now be made to a bolus throughout the remainder of this specification.

The bolus has an external covering. In some embodiments of the present invention, the external covering may be a wax or resin coating, but in preferred embodiments of the present invention, the external covering is a housing. Reference shall now be made to the bolus having a housing throughout the remainder of this specification.

The housing of the bolus may be a plastic or alloy casing, or a combination of both, which is biologically inert. This ensures that there is no harm to the animal should the bolus housing be retained in the rumen rather than be excreted.

Preferably, the housing of the bolus is closed at one end using an end cap. Alternatively, the housing may have been fabricated with a closed end which is integral with the housing. This is to ensure that erosion of the dosage media occurs only at the open end of the bolus.

The dosage media may be in the form of capsules or the like with a gelatin type coating or shell protecting the substance. Alternatively, the dosage media may be granules of substance separated by internal partitions in the bolus housing.

Preferably, the dosage media is in the form of solid tablets, and reference shall now be made to tablets throughout the remainder of this specification.

The substances within the tablets may vary according to the condition being treated. However, in a preferred embodiment of the invention, the substances may include anthelmintics compounds, such as abamectin and ivermectin which is used to control parasitic infestation.

However, it should be understood that the use of the bolus with these anthelmintics is not intended to be limiting, and persons skilled in the art will appreciate that a wide variety of substances may be used with the present invention. For example, the present invention may also be used for delivery of nutrients and essential elements.

Reference shall now be made to the substances being an active agent throughout the remainder of this specification.

The tablets of the present invention are successively larger than the preceding tablet.

This means that the physical size and/or the amount of active agent contained in each tablet is greater than the preceding tablet.

Preferably, the size of the tablet increases with each successive tablet. This is preferred as a single mixture may be used to manufacture the bolus tablets. Alternatively, it may that several mixtures are used to make the bolus tablets, each mixture containing varying concentrations of active agents. However, persons skilled in the art will appreciate that this greatly complicates manufacture of the bolus tablets.

It is also envisaged that the tablet sizes may also compensate for sexual dimorphism in treated animals. In many animal species, it is common for the male to be larger than a female, even though the animals may be the same age. In this embodiment, the mixtures and sizes for the bolus tablets may be more concentrated or larger if the animal to be treated is a male.

Of course, it will be appreciated that in some species, sexual dimorphism favours the female, or there may be no sexual dimorphism at all, which can be compensated for through tablet mixtures and sizes.

As may be appreciated as those skilled in the art, it may be important that the rate of erosion from the tablets be maintained in an approximately constant rate.

A faster than average erosion rate or breakdown of the tablet may be harmful to the animal being treated.

If the erosion rate is too slow, the animal may receive insufficient active agent for the application required. For some agents such as anthelmintics, low dosage can result in the development of drug resistance in the targeted parasites or bacteria.

In preferred embodiments of the present invention, the erosion rate of the bolus housing the tablets is approximately 0.5 mm/day. However, persons skilled in the art will appreciate that this is not meant to be limiting, and the erosion rate of the bolus may be higher or lower depending on the construction of the bolus, and the desired dosage rate for the animal to be treated.

In preferred embodiments of the present invention, each successive active containing tablet may be interspaced with a blank or non-active containing tablet.

In this embodiment of the present invention, the blank tablets are preferably formed from graphite. Additional components may be included, such as iron or other elements. However, persons skilled in the art will appreciate that other materials may be used for manufacturing the blank tablets. For example a tablet consisting of a starch base may be used for this purpose.

It will be appreciated that in this embodiment of the invention, the active agent is released on a pulse basis rather than a continuous basis.

The present invention compensates for growth rates in juvenile cattle by incremental dosing. As the size of the animal increases, the total amount of active agents in the circulatory system of the animal also increases, but is proportional to the weight of the animal.

The present invention also reduces the number of times which a particular animal needs to be dosed. Treating a young animal with an incremental dosage rate that compensates for growth of the animal means that one bolus can treat the animal for several months.

There is no need to bring the animal back to a dosage area such as a cattle yard for repeated dosing. This allows the animals to grazed quite remotely from the dosage area for extended periods of time.

It should be appreciated from the above description that there is provided a bolus and method of treating an animal that attempts to solve the problem of compensating for growth rates in animals being treated for specific conditions.

BRIEF DESCRIPTION OF DRAWINGS

Further aspects of the present invention will become apparent from the following description which is given by way of example only and with reference to the accompanying drawings in which.

BEST MODES FOR CARRYING OUT THE INVENTION

Figure 1:
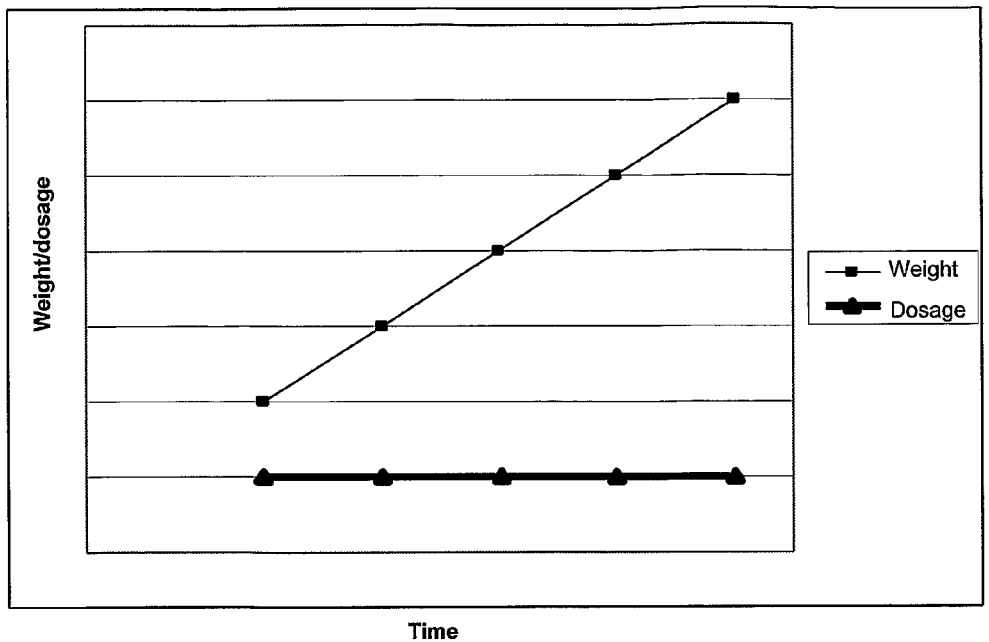
FIG. 1 shows a graph of cattle weight and dosage released by a conventional bolus with respect to time.

As shown in FIG. 1, a conventional bolus, which has tablets which are the same in size and ingredients, does not compensate for the growth of the treated animal with time.

It can be appreciated that the dosage levels remain at a static level, which can be inappropriate when the animal is either in a very juvenile stage (and potentially may be receiving dosages more appropriate for an adult) or an adult stage (and may potentially be receiving dosages more appropriate for an animal of lesser body mass.

Figure 2:
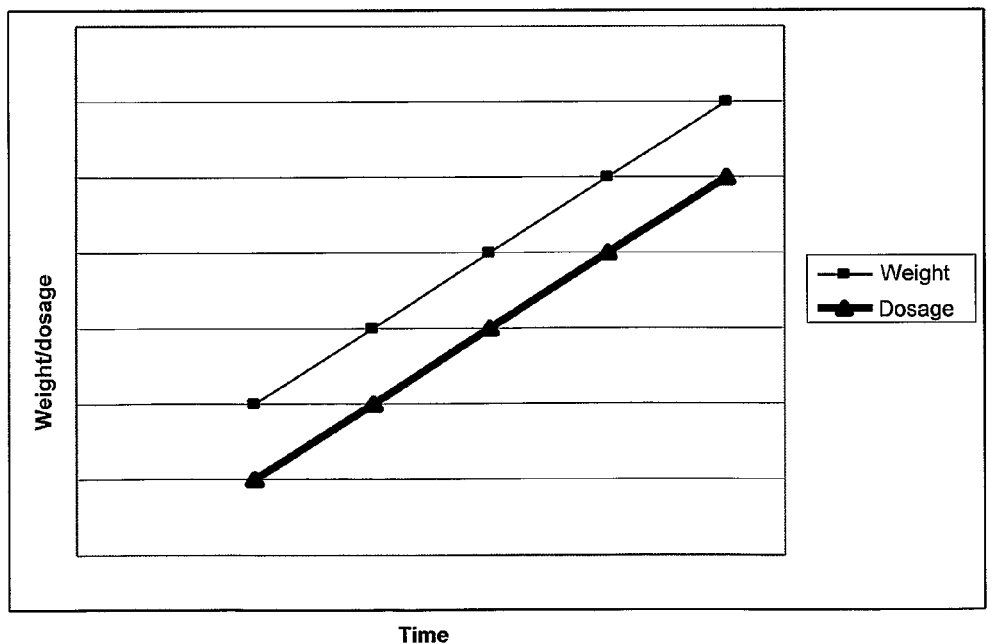
FIG. 2 shows a graph of cattle weight and dosage released by the present invention with respect to time.

This is in contrast to the present invention, as demonstrated by FIG. 2.

Here, it can be seen that as the weight (and therefore size) of the treated animal increases, the dosage rates also increase. This keeps the dosage constant with respect to the animal's body mass.

Figure 3:
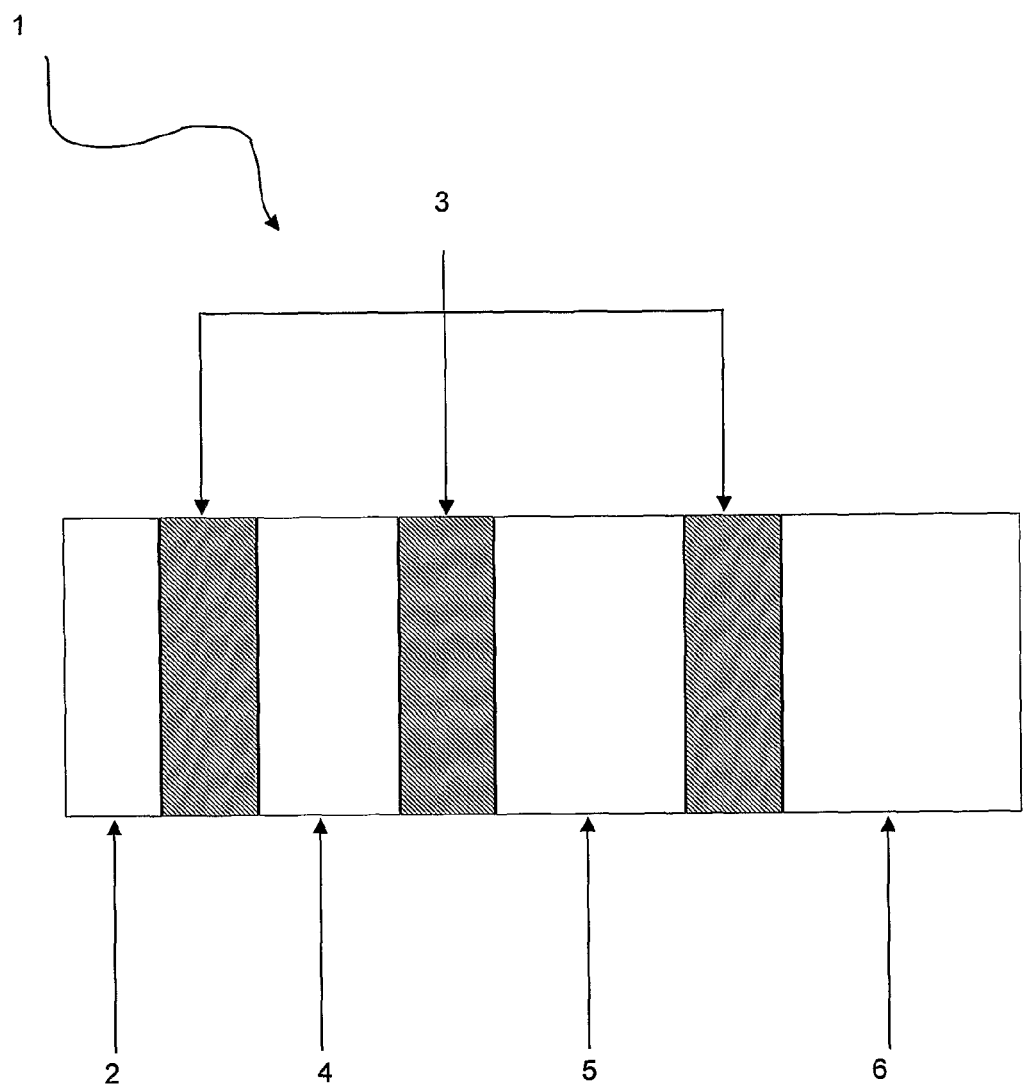
FIG. 3 shows a side view of the present invention.

This is achieved through the use of a series of tablets which gradually increase in size, as illustrated in FIG. 3.

FIG. 3 depicts the tablet core (generally indicated by arrow 1) which is retained in a bolus housing (not shown).

The first tablet (2) is followed by a graphite spacer (3). The following tablets (4, 5, and 6) are each successively larger than the preceding tablet. Interspersed between each tablet is a graphite spacer (3), although these are optional.

Erosion begins from the open end of the bolus housing, acting upon the first tablet (2) in the tablet core. When the bolus housing (not shown) and tablet (2) is completely eroded, the first graphite spacer (3) is exposed to the eroding medium.

The use of graphite spacers (3) means the dosage is more pulsed, rather than a continual release which would be the case in a bolus which has no spacers.

Following erosion of the first graphite spacer (3), the next, larger tablet (4) is eroded.

Erosion rates of the tablets (2, 4, 5, 6) and spacers (3) approximates 0.5 mm a day, so it can be appreciated that the time period between delivery of the bolus and therefore the medicament contained in the eroded tablet (2) and the initiation of the subsequent tablet (4) may be in the order of months.

In the meantime, the treated animal has steadily grown and therefore shows an increased body mass relative to when the animal was first treated.

The subsequent tablet (4) is larger than the preceding tablet (2) to compensate for this increase in body mass.

The invention is now described with reference to an example of tablet preparations and formulations.

EXAMPLE 1

Preparation

Abamectin is dissolved in benzyl alcohol and then mixed in monopropylene glycol. The resulting mixture is further mixed with Levamisole hydrochloride, povidone and corn starch.

The preparation is then dried at 40° Celsius. Once drying is completed, sodium starch glycolate, Aerosil 200 and magnesium sterate is added.

The resulting tablet disintegrates in water held at 37° Celsius within 15 minutes.

Formulation

Reviewing the proportions of the ingredients used in this example, it can be appreciated that the proportions increase as the body mass of the animal increases.

The initial tablet is 15 mm in thickness, and each successive tablet progressively increases in size.

| Ingredients | Quantity per tablet (mg) | | | |
|---|---|---|---|---|
| | Cattle 150 kg | Cattle 175 kg | Cattle 200 kg | Cattle 250 kg |
| Abamectin | 63 | 73.5 | 84 | 105 |
| Monopropylene glycol | 126 | 147 | 168 | 210 |
| Benzyl alcohol | 60 | 70 | 80 | 100 |
| Levamisole hydrochloride | 1200 | 1400 | 1600 | 2000 |
| Povidone | 12 | 14 | 16 | 20 |
| Corn starch | 600 | 700 | 800 | 1000 |
| Sodium starch glycolate | 175 | 204 | 233 | 291 |
| Aerosil 200 | 40 | 47 | 53 | 67 |
| Magnesium sterate | 49 | 57 | 65 | 82 |
| Total tablet weight | 2325 | 2712.5 | 3099 | 3875 |

Results

The increased proportions of active, in this case Abamectin and Levamisole, in each successive tablet are important in treating for internal parasites, while at the same time compensating for the growth of the animal.

This ensures that dosage rates when the animal is a juvenile is more appropriate and less likely to have detrimental health effects on the animal.

Gradually increasing the dosage rate as the animal grows also means that is unlikely that any parasites residing in the gut of the animal will develop resistance to the anthelmintic of choice.

Aspects of the present invention have been described by way of example only and it should be appreciated that modifications and additions may be made thereto without departing from the scope of the appended claims.

What we claim is:

1. A bolus for administration of an active substance to an animal, the bolus including
   a housing, and
   a core inside the housing wherein the core is formed from a plurality of tablets, wherein each tablet contains an active substance, wherein the tablets are separated from each other within the housing by a degradable barrier
   the bolus characterised in that
   the thickness of each successive tablet increases relative to the preceding tablet while the circumference remains the same such that the amount of active substance released by each tablet is progressively more than the amount of active substance released by the previous tablet.

2. A bolus as claimed in claim 1 wherein the active substance in each successive tablet increases relative to the preceding tablet.

3. A bolus as claimed in claim 1 wherein the active substance includes at least one anthelmintic.

4. A bolus as claimed in claim 1 wherein the active substance includes at least one essential element.

5. A bolus as claimed in claim 1 wherein the active agent includes at least one nutritional supplement.

6. A bolus as claimed in claim 1 wherein the animal is a ruminant.

7. A method of constructing a bolus for delivering an active substance to an animal, the bolus including a housing, and a core inside the housing wherein the core is formed from a plurality of tablets, wherein each tablet contains an active substance, wherein the tablets are separated from each other within the housing by a degradable barrier, wherein the thickness of each successive tablet increases relative to the preceding tablet while the circumference remains the same such that the amount of active substance released by each tablet is progressively more than the amount of active substance released by the previous tablet, the method of construction characterised by the steps of:

a) inserting a tablet into the housing, and then b) inserting a degradable barrier into the housing, and c) repeating steps a) and b) until the bolus is assembled.

8. A method of treating a non-human animal, including the steps of, a) placing a bolus in an non-human animal's stomach, wherein the bolus contains an active substance in the form of a plurality of tablets, and wherein each tablet is separated from its neighbouring tablets by a biodegradable barrier, and b) releasing the tablets and biodegradable barriers sequentially in the non-human animal's stomach, and wherein the tablets chosen for delivery are ordered within the bolus such that the ratio of active substance released by the bolus at a particular time to the estimated body mass of the non-human animal at that time remains substantially constant.

9. A method of treating a non-human animal as claimed in claim 8 wherein the animal is a ruminant.

* * * * *